United States Patent [19]

Yamamoto et al.

[11] Patent Number: 5,406,406
[45] Date of Patent: Apr. 11, 1995

[54] MOLECULAR CRYSTAL AND WAVELENGTH CONVERSION DEVICES USING THE SAME

[75] Inventors: Hironobu Yamamoto, Yokohama; Satoru Funato; Kaoru Okaniwa, both of Kawagoe, all of Japan

[73] Assignee: Hoechst Aktiengesellschaft, Frankfurt am Main, Germany

[21] Appl. No.: 228,093

[22] Filed: Apr. 15, 1994

[30] Foreign Application Priority Data

Apr. 19, 1993 [JP] Japan .................................. 5-091605

[51] Int. Cl.⁶ ................................................. G02F 1/35
[52] U.S. Cl. .................................... 359/326; 252/582; 359/332; 385/122; 385/143
[58] Field of Search .................... 359/326–332; 372/21, 22; 385/122, 141, 143; 252/582, 584, 586–589

[56] References Cited

U.S. PATENT DOCUMENTS 3,948,893  4/1976  Aichinger et al. ................ 544/221
3,970,752  7/1976  Aichinger et al. ................ 514/241

*Primary Examiner*—John D. Lee
*Attorney, Agent, or Firm*—Curtis, Morris & Safford

[57] ABSTRACT

An organic molecular crystal comprising the compound N-isopropyl-N'-(4-acetylphenyl)-urea is used for preparing an optical wavelength conversion device. Especially, the device may comprise a core and a clad wherein the organic crystal is used as the core.

6 Claims, 8 Drawing Sheets

MOLECULAR CRYSTAL AND WAVELENGTH CONVERSION DEVICES USING THE SAME

BACKGROUND OF THE INVENTION

This invention relates to nonlinear optical materials useful for wavelength conversion or parametric amplification of laser light in the fields of optical communication and optical information processing. More particularly, this invention relates to a molecular crystal useful for a nonlinear optical material. The invention also relates to methods and devices for performing wavelength conversion of laser light using the molecular crystal as a nonlinear optical material.

Nonlinear optical materials are today drawing increasing attention in the field of opto-electronics. Nonlinear optical materials are those materials which interact with light to exhibit a nonlinear optical response. Second-order nonlinear optical effects are exemplified by second harmonic generation (SHG) and the first-order electro-optical (EO) effect (Pockel's effect). The materials exhibiting these effects can be utilized to various devices such as frequency doubling of the laser light, electro-optical modulation and electro-optical switching. Continuative efforts, therefore, are being made to study nonlinear optical devices exhibiting these effects.

Nonlinear optical materials conventionally known to exhibit the SHG effects are inorganic substances such as lithium niobate ($LiNbO_3$) and potassium titanyl phosphate (KTP). The studies heretofore made on wavelength conversion devices utilizing the SHG effect have also focused on these inorganic substances. In recent years, however, organic nonlinear optical materials having a conjugated $\pi$-electron system have drawn the increasing attention because of their large optical nonlinearity and fast optical response, and many studies are being conducted in a search for promising materials.

Conventionally known organic nonlinear optical materials include urea, 2-methyl-4-nitroaniline (MNA), m-nitroaniline, N,N-dimethyl-2-acetylamino-4-nitroaniline (DAN), 3-methyl-4-nitropyridine-N-oxide (POM) and N-(4-nitrophenyl)-(L) (NPP). Details about organic nonlinear optical materials may be found in, for example, (1) "Nonlinear Optical Properties of Organic and Polymeric Materials", ed. David J. Williams, ACS Symposium Series No. 233 (1983);
(2) "Nonlinear Optical Properties of Organic Molecules and Crystals", Vols. 1 and 2, ed. D. S. Chemla and J. Zyss, Academic Press (1987);
(3) "Yuki Hisenkei Kogaku Zairyo (Organic Nonlinear Optical Materials)", Masao Kato and Hachiro Nakanishi, CMC Press (1985); and
(4) "Shin-Yuki Hisenkei Kogaku Zairyo (Advanced Nonlinear Optical Organic Materials)" Vols. I and II, T. Kobayashi, M. Umegaki, H. Nakanishi and N. Nakamura, CMC Press (1991).

The nonlinearity of organic substances having a conjugated $\pi$-electron system is caused by the nonlinear polarization that occurs due to the interaction between laser light and the delocalized $\pi$-electrons in the organic molecule of interest. In order to enhance the nonlinear polarization or the hyperpolarizability $\beta$ of the molecule, an electron-donating group (donor) or an electron-attractive group (acceptor) is introduced into the conjugated $\pi$-electron system as a common technique for molecular design.

An issue with the organic compound synthesized by this molecular design technique is that it generally has a large dipole moment. Hence, owing to the dipole-dipole interaction, this organic compound tends to form a crystal having a centrosymmetric structure in the course of crystallization, in which the dipole moments of adjacent molecules cancel out each other. In this case, the SHG effects will no longer be observed. It is technically impossible, to date, to predict the crystal structure of a certain compound from its chemical structure. Therefore, in order to produce crystals having no centrosymmetric structure, empirical techniques are currently being employed, as exemplified by introducing an optically active group (chirality) or hydrogen bond into the conjugated $\pi$-electron system or reducing the dipole moment of the molecule at the ground state so as to reduce the dipole-dipole interaction.

It should also be mentioned that compounds that experience a substantial charge transfer between a donor and an acceptor will shift the absorption maximum to longer wavelength, which results in the extension of the absorption wavelength region to the visible range. For the case of a wavelength conversion device combined with a semiconductor laser operating at 780–840 nm, the device will show the deterioration if it absorbs the light of the SHG wavelength of from 390 to 420 nm. Therefore, it is preferred for the materials of wavelength conversion devices to have an absorption at wavelengths shorter than that of SHG of the fundamental wavelength and thus it means that a cut-off wavelength ($\lambda_{cut\ off}$) of 390 nm or shorter in the nonlinear optical materials is suitable for the application.

The inorganic nonlinear optical materials currently used in practical applications as exemplified by lithium niobate and KTP have the disadvantage that they are expensive while their performance for the wavelength conversion generally is not as good as that of organic materials. On the other hand, organic nonlinear optical materials have the advantage that they are inexpensive for material cost and can be synthesized fairly easily. However, generally speaking, the absorption wavelength range of such organic nonlinear optical materials, if they exhibit high conversion efficiency, extends to the visible wavelength region, and thus their crystals show a yellow or orange color. This means that those materials absorb the SH light of semiconductor lasers, and are unsuitable for the wavelength conversion devices.

Further, the organic nonlinear optical materials have the disadvantage of difficulty in obtaining large single crystals or fabricating waveguide-type wavelength conversion devices such as fiber waveguide-type, and slab and channel waveguide-type wavelength conversion devices. When fabricating a waveguide-type wavelength conversion device that employs an organic molecular crystal, the molecular arrangement in the crystal is important. In order to enhance the operating efficiency of the wavelength conversion device, the molecules must be aligned in such a direction that the nonlinear optical performance of the crystal can be effectively brought out. Therefore, in order to fabricate a high performance wavelength conversion device, the molecular arrangement in the single crystal must be taken into account.

While practically feasible organic nonlinear optical materials should possess various characteristics, the following are particularly important:

1) large optical nonlinearity;
2) high transparency in the operating wavelength range, in particular, which is longer than 390 nm;
3) high single crystallinity, leading to the production of single crystals of high quality;
4) high mechanical strength to assure ease in crystal processing or in the fabrication of waveguides;
5) thermal and chemical stability;
6) controlled crystal growth in such a manner that molecules are aligned in such a direction that the nonlinear optical performance of the crystal can be effectively brought out when fabricating a bulk-type or waveguide-type wavelength conversion device.

None of the organic nonlinear optical materials known to date have been found to be promising since they do not satisfy all of these performance requirements.

SUMMARY OF THE INVENTION

Under the circumstances, it is a first object of the present invention to provide an organic molecular crystal which has light absorption at wavelengths shorter than 390 nm, which has good crystallinity and processability, which has a molecular arrangement which is free from centrosymmetry and which hence is suitable for use in wavelength conversion devices.

A second object of the present invention is to provide a method for wavelengths conversion using said organic molecular crystal.

A third object of the present invention is to provide a fiber waveguide-type wavelength conversion device which employs an organic crystals as a core of the fiber.

A fourth object of the present invention is to provide a slab or channel waveguide-type wavelength conversion device which employs an organic crystal and which assures high efficiency in conversion of wavelength of light at the visible range.

A fifth object of the present invention is to provide an optical wavelength conversion device employing said organic molecular crystal which is capable of modulating the intensity of light.

The inventors of the present invention have found that the above objects can be achieved by an organic molecular crystal of a compound represented by the following formula (I):

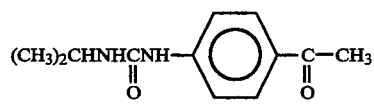
(I)

The compound of the formula (I) is N-isopropyl-N'-(4-acetylphenyl) urea and can generally be synthesized by the following method: isopropyl isocyanate is reacted with 4-aminoacetophenone under reflux in a solvent such as tetrahydrofuran in the presence of a basic catalyst such as triethylamine.

Particularly preferred crystal of the formula (I) is monoclinic and space group of $P2_1$.

BRIEF DESCRIPTION OF THE DRAWINGS

The present invention is described below in detail with reference to the accompanying drawings, in which.

DETAILED DESCRIPTION OF THE INVENTION

Figure 1:
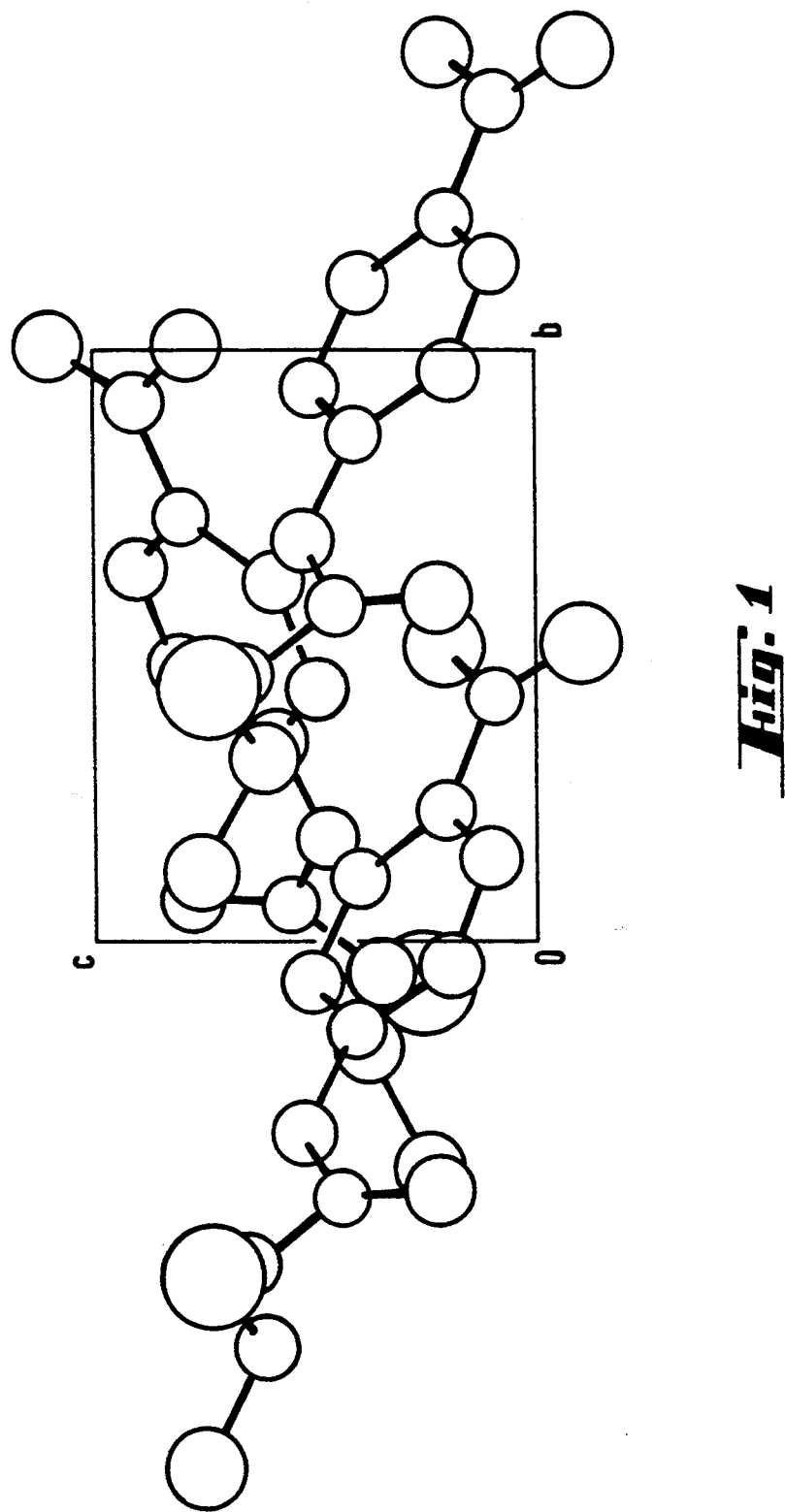
FIG. 1 shows a crystal structure of the compound of the formula (I) as it is projected in the direction of the a axis.

To obtain the single crystal of the compound of the formula (I), any of the techniques for crystallization known in the art may be used, including crystallization from a solvent, at the vapor phase or from a melt. Solvents which can be used include: water; alcohols such as methanol and ethanol; ketones such as acetone, methyl ethyl ketone and methyl isobutyl ketone; acetonitrile, tetrahydrofuran, chloroform, dichloromethane, dimethyl sulfoxide, dimethylformamide and dimethylacetamide. The use of water, acetone or acetonitrile is particularly preferred. For details about single crystal growth techniques, reference should be made to "Kessho Ikusei Kiso Gijutsu (Fundamentals of Crystal Growth Technology)" by S. Takasu, Tokyo University Press, 1980, and "Kessho Kogaku Handobukku (Crystal Engineering Handbook)", Kyoritsu Publishing, 1971.

The compound of the formula (I) may be partly or wholly deuterated. Alternatively, the compound of the formula (I) may be used in combination with a partially or wholly deuterated compound thereof.

What is particularly advantageous about the molecular crystal of the compound of the formula (I) is that desired crystal forms such as a thin plate can be produced very easily by controlling the crystal growth conditions such as the temperature and concentration of the solvent used. The thus produced thin, planar crystal will exhibit a large d tensor ($d_{22}$) within the major plane of the crystal. By controlling the crystal growth conditions, the thickness of the crystal can be adjusted to a value ranging from several to several hundred microns. The single crystal of such a crystal form is very advantageous in fabricating an optical wavelength conversion device, in particular, a slab or channel waveguide-type optical wavelength conversion device. As described in M. Umegaki, "Yuki Hisenkei Kogaku Zairyo (Organic Nonlinear Optical Materials)", Bunshin Publishing (1990), the thickness of crystal in an optical waveguide must be controlled with extremely high precision, particularly in the case where the SHG is achieved by mode-mode phase matching. The molecular crystal of the present invention can be processed by etching to a desired thickness with extremely high precision. Illustrative etching techniques include liquid-phase etching using a mixed solvent system of acetone and acetonitrile, solvent etching, chemical etching and reactive ion etching (RIE). The precise controllability of the crystal thickness has the potential for not only achieving mode-mode phase matching but also accomplishing lateral or transverse phase matching. See T. Kondo and R. Ito, "Oyo Butsuri (Applied Physics)", Vol. 61, No. 9, p. 910 (1992). This means that the overlap integral between an electric field of the fundamental wave and that of the second harmonic wave can be large, eventually producing the second harmonic wave with high intensity.

The present invention also provides a nonlinear optical material comprising the above-mentioned organic molecular crystal. According to another aspect of the present invention, a fiber waveguide-type optical wavelength conversion device which comprises a core and a clad may be fabricated with the molecular crystal of the invention which is used as the core. The clad may be made of any material having a smaller refractive index than the core. Exemplary materials for clad include inorganic substances such as glass and organic substances such as a photocurable adhesive.

According to the present invention, there are provided a planar waveguide-type optical wavelength conversion device in which the molecular crystal of the invention is used as a waveguiding layer, and a fiber waveguide-type optical wavelength conversion device in which the molecular crystal of the invention is used as a core. In these optical wavelength conversion devices, the conversion of wavelength of laser light is achieved either by mode-mode phase matching using mode dispersion in the waveguide or by the Cherenkov radiation. To this end, the molecular crystal of the invention is processed in such a manner that the a or c axis of the crystal is aligned along the direction of wave propagation. As for the light source, linearly polarized fundamental wave is introduced in a direction parallel to the b axis of the crystal.

A slab or channel waveguide-type optical wavelength conversion device employing the molecular crystal of the invention is advantageous in view of the optical coupling when it is used with a semiconductor laser since the tensor $d_{22}$ is parallel to the major plane of the crystal. More specifically, the semiconductor laser is in TE mode, and this mode is advantageous for achieving large nonlinearity in the waveguide. Therefore, it is not necessary to rotate the polarization of the semiconductor laser when the semiconductor laser light is coupled into the waveguide-type optical wavelength conversion device. In other words, the semiconductor laser can be coupled directly into the device of the present invention.

One of the major potential applications of the optical wavelength conversion device is as a light source for optical recording. In optical recording, there is a particular need for modulation of light. The higher the modulation frequency, the broader the scope of potential applications. The principal advantage of the optical wavelength conversion device as a light source for optical recording is due to possibility of modulation of the second harmonic wave by providing suitable electrodes in the optical wavelength conversion device. Materials having second-order nonlinearity are generally characterized not only by their ability to generate second harmonics but also by the possibility of modulation for their refractive indices by the applied electric field. The latter contributes to the enhancement of the intensity of the second harmonic wave under the conditions suitable for mode-mode phase matching. In other words, an optical wavelength conversion device being capable of modulation can be provided. To this end, there is provided a waveguide-type optical wavelength conversion device which has a pair of electrodes provided on opposite sides of the core in the optical wavelength conversion device. Such an optical wavelength conversion device enables to adjust the conditions for phase matching and to perform modulation of the second harmonic wave.

In the present invention, wavelength conversion is in no way limited to the generation of second harmonics and it may be effected to generate third harmonics and optical mixing of two frequencies.

The fundamental wave to be subjected to wavelength conversion may be emitted from a wide range of laser light sources, including semiconductor lasers such as InGaAsP and AlGaAs lasers, solid lasers such as Nd:YAG and Ti:sapphire lasers and various dye lasers.

The molecular crystal of the present invention permits high transmittance of blue-colored light and has noncentrosymmetric molecular arrangement in the crystal; therefore, it has nonlinear optical effects of the second order. The fiber waveguide-type optical wavelength conversion device of the present invention is very easy to fabricate and, hence, provides a particular advantage in the process of commercial production. As a further advantage, the optical interaction length of the optical wave conversion device can be sufficiently increased to achieve high efficiency of wavelength conversion. In addition, a thin, planar crystal can be formed with comparative ease by suitable selection of the crystal growth conditions. Furthermore, the crystallographic orientation is such that a large d tensor exists in the major plane of the planar crystal and, hence, a slab and a channel waveguide-type optical wavelength conversion device can be fabricated very easily. Yet another advantage is that the thickness of the crystal can be controlled at a desired value with high precision by employing etching techniques and, hence, it becomes possible to effect mode-mode phase matching, thereby achieving high SHG intensity. If necessary, a pair of electrodes may be provided to the waveguide-type optical wavelength conversion device, thereby adjusting the phase matching conditions and performing modulation of light.

The present invention will be understood more readily with reference to the following examples; however these examples are intended to illustrate the invention and are not to be construed as limiting the scope of the invention.

EXAMPLE 1

N-Isopropyl-N'-(4-acetylphenyl) urea, the compound of the formula (I), was prepared by the following procedure. Twenty-seven grams of 4-aminoacetophenone was charged into a flask (200 ml) equipped with a stirrer and a condenser. Tetrahydrofuran (100 ml) and a catalytic amount of triethylamine were then charged into the flask. The mixture was stirred until 4- aminoacetophenone dissolved completely to form a solution. Isopropyl isocyanate (23 ml) was added dropwise to the solution, and the solution was refluxed in an oil bath for several hours. After confirming the completion of the reaction by TLC, the refluxing was stopped and the solution was concentrated. The precipitated crystal was filtered, washed first with hexane and then with water, and recrystallized from acetone. As a result, a white crystal was obtained in an amount of 45 g and the yield was 95% or more. The compound thus obtained was identified by the measurements of melting point and NMR.

Melting point: 149° C.

H-NMR: (DMSO, TMS as standard) δ: 1.12(6H,d), 2.49(3H,s), 3.75(1H,m), 6.17(1H,d), 7.51(2H,d), 7.86(2H,d), 8.73(1H.s)

The compound was further subjected to recrystallization to produce a powder having a purity of at least 99.9% (as analyzed by HPLC). The powder was dissolved in acetone or methanol and the resulting solution was cast on a slide glass. The slide glass was left to stand overnight at a room temperature, whereby the solvent was evaporated to give a thin, planar single crystal. The single crystal had a dimension of about 2 mm×5 mm, with the thickness ranging from about 1 to 10 microns. The crystallographic structure of the single crystal was analyzed by means of a four-axis X-ray diffractometer with CuKα. The following crystallographic data were obtained.

| Crystal system: | monoclinic |
|---|---|
| Space group: | P2$_1$ |
| Point group: | 2 |
| Lattice constants: | a = 18.645 Å |
| | b = 6.539 Å |
| | c = 4.900 Å |
| | β = 96.54° |
| | Z = 2 |

Figure 2:
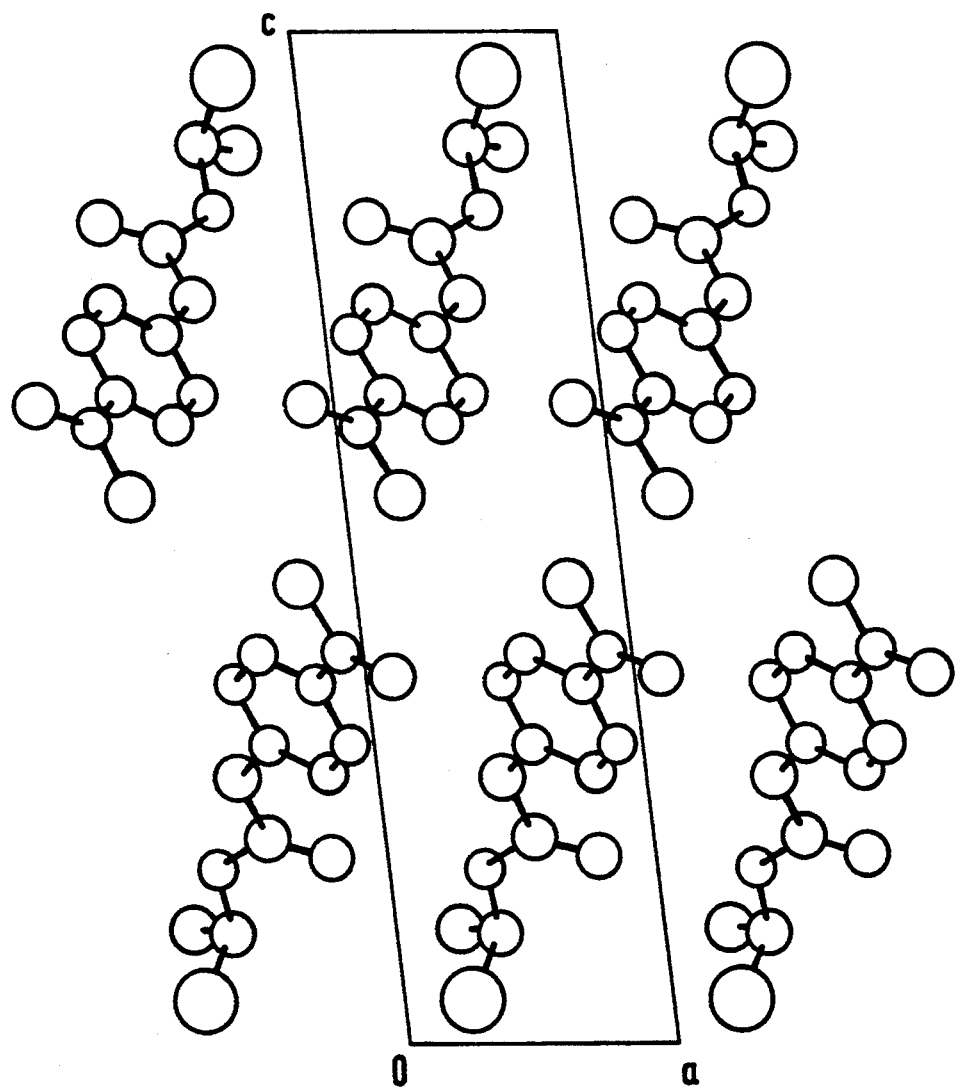
FIG. 2 shows a crystal structure of the compound of the formula (I) as it is projected in the direction of the b axis.
Figure 3:
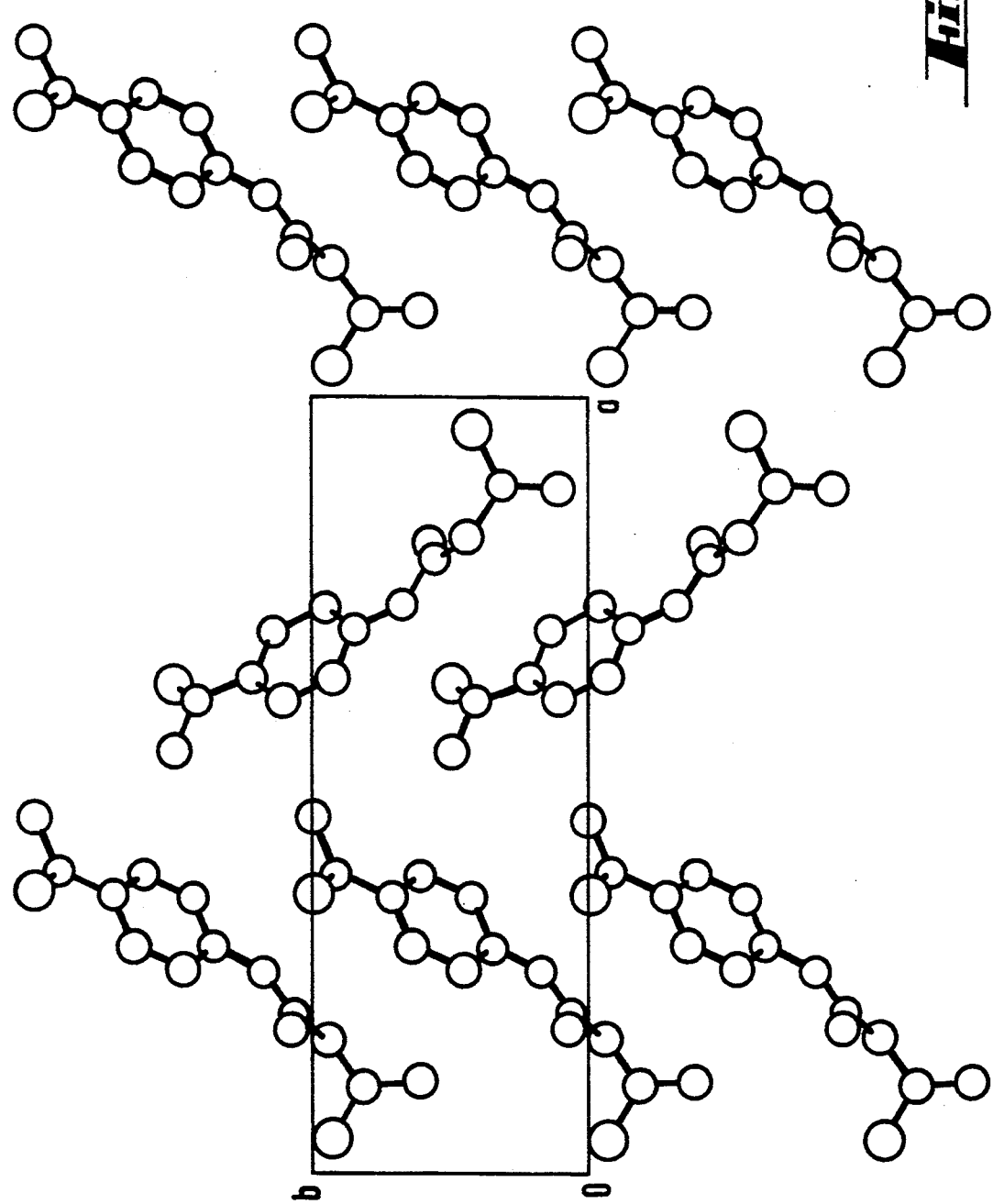
FIG. 3 shows a crystal structure of the compound of the formula (I) as it is projected in the direction of the c axis.

The crystal structures as observed in the directions of three principal axes are shown in FIGS. 1 to 3. The space group P2$_1$ indicates that the crystal under consideration has noncentrosymmetric system.

Miller index of the major surface of the single crystal was evaluated from the crystallographic data listed above and was found to be (100). It will be understood from the result that the molecules of the formula (I) were arranged parallel to the (100) plane.

The single crystal of the compound of formula (I) is of monoclinic system and belongs to point group 2 and, hence, the tensor elements of a second-order nonlinear optical constant d can be expressed by:

$$d = \begin{pmatrix} 0 & 0 & 0 & d_{14} & 0 & d_{16} \\ d_{21} & d_{22} & d_{23} & 0 & d_{24} & 0 \\ 0 & 0 & 0 & d_{34} & 0 & d_{36} \end{pmatrix}$$

where $d_{21}$ is a nonlinear optical constant for the case where light which is linearly polarized to the X axis of the crystal (Y and Z are the other principal axes) is introduced into the crystal as a fundamental wave (the polarization is hereunder referred to as "X polarization" and similar designations will be used for polarization in Y and Z directions) to generate the second harmonic wave of Y polarization. Similarly, $d_{22}$ is a nonlinear optical constant for the case where a fundamental wave of Y polarization is launched to generate the second harmonic wave of Y polarization. The single crystal obtained in Example 1 has the Y axis within the (100) plane, thus enabling refractive index measurement in the direction of Y axis and this is why $d_{22}$ was measured (the result is shown in Example 5 which follows).

EXAMPLE 2

The procedure in Example 1 was repeated on the powder prepared in Example 1, except that the solvent acetone was replaced by acetonitrile. As in Example 1, a thin, planar single crystal was obtained.

The same powder was dissolved in acetone, acetonitrile and water under heating and thereafter cooled slowly to produce similar single crystal.

The crystallographic structures of the four kinds of single crystals were examined by X-ray diffraction. All of them were found to be of the same crystal system as the single crystal obtained in Example 1.

EXAMPLE 3

Figure 4:
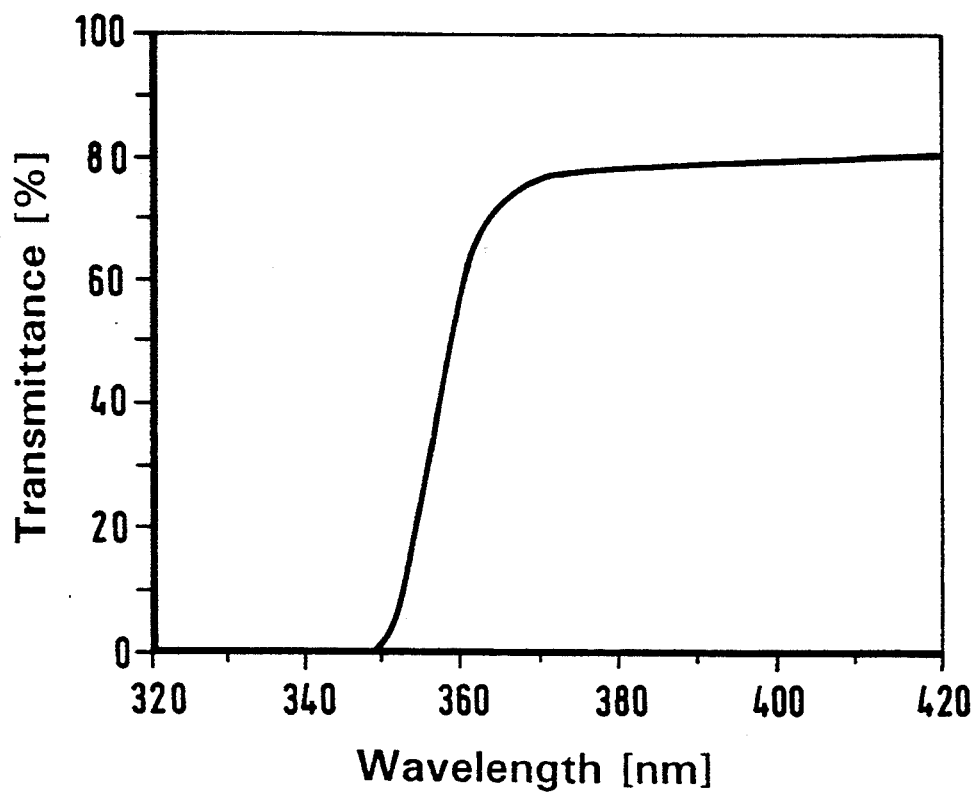
FIG. 4 is a UV-VIS transmittance spectrum for the crystal of the compound of the formula (I)

The compound of the formula (I) was prepared by the same procedure as used in Example 1. The compound was dissolved in acetone and a planar crystal of a few millimeters thick was obtained by evaporating the solvent. A UV-VIS spectrum of the crystal was measured to determine the optical absorption cutoff wavelength. The results are shown in FIG. 4, from which it can be seen that the crystal of interest had an optical absorption cut-off wavelength ($\lambda_{cut\,off}$) of 380 nm, demonstrating that it did not cause the absorption of the second harmonic wave at a practical wavelength range.

EXAMPLE 4

The refractive index of the crystal of the compound of the formula (I) was measured by the liquid immersion (Becke line) method. For details of the liquid immersion method, see "Kogaku Gijutsu Handobukku (Handbook of Optical Technology)", Enlarged Ed. by H. Kubota, Y. Ukita and G. Aida, Asakura Publishing (1975). Light from a xenon arc lamp was passed through a monochromator to produce a monochromatic radiation, which was used as incident light for refractive index measurement. The incident light was launched along Y axis of the crystal and the measurement was carried out at four points in the visible wavelength range. The results of the measurement were corrected for the immersion liquid used. The refractive indices at wavelengths of 532 nm and 1064 nm were calculated from the corrected data by using Sellmeir's equation. The refractive index in the direction of Y axis at the wavelength 532 nm was 1.781 whereas the refractive index in the same direction at the wavelength 1064 nm was 1,699.

Figure 5:
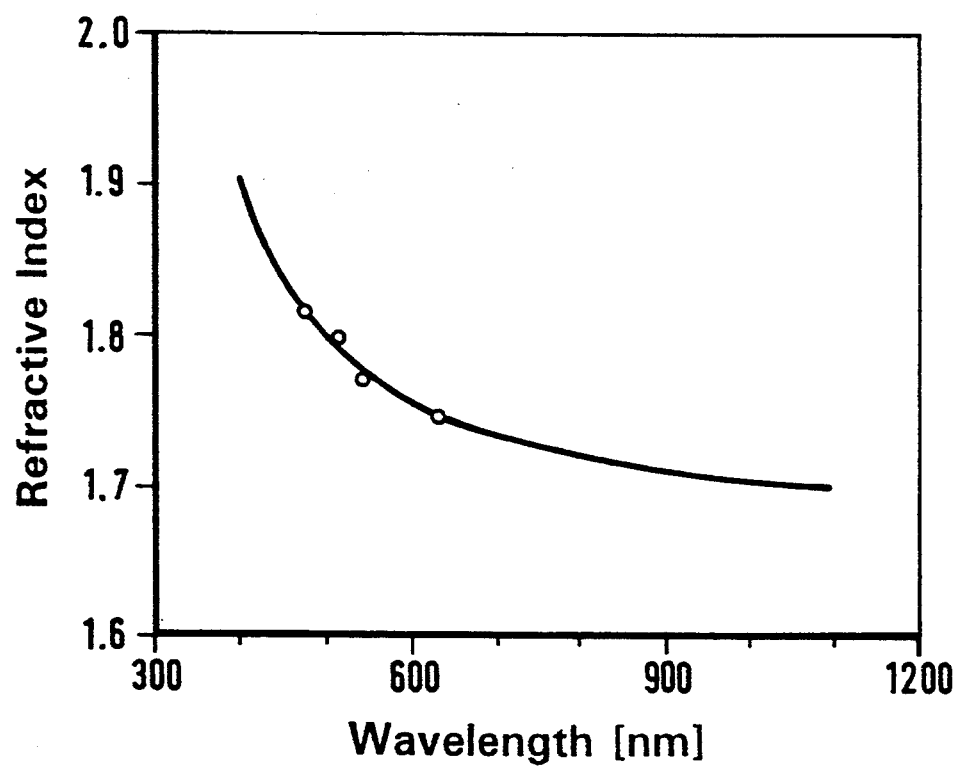
FIG. 5 is shows a refractive index dispersion curve of $n_y$ of the compound of the formula (I) as a function of wavelength.

The results of refractive index measurement are shown in FIG. 5, in which the small circles indicate the observed values and the solid line is the fitting curve theoretically calculated from Sellmeir's equation. The wavelength-dependent dispersion of refractive index was rechecked by the polarized reflection spectrum of the single crystal of compound (I) and its analysis using Kramers-Kronig relations. The results confirmed the validity of the refractive index dispersion illustrated in FIG. 5.

EXAMPLE 5

The nonlinear optical coefficient $d_{22}$ of the crystal of compound (I) was measured by using the rotating Maker fringe method. For details of this method, see J.

Figure 6:
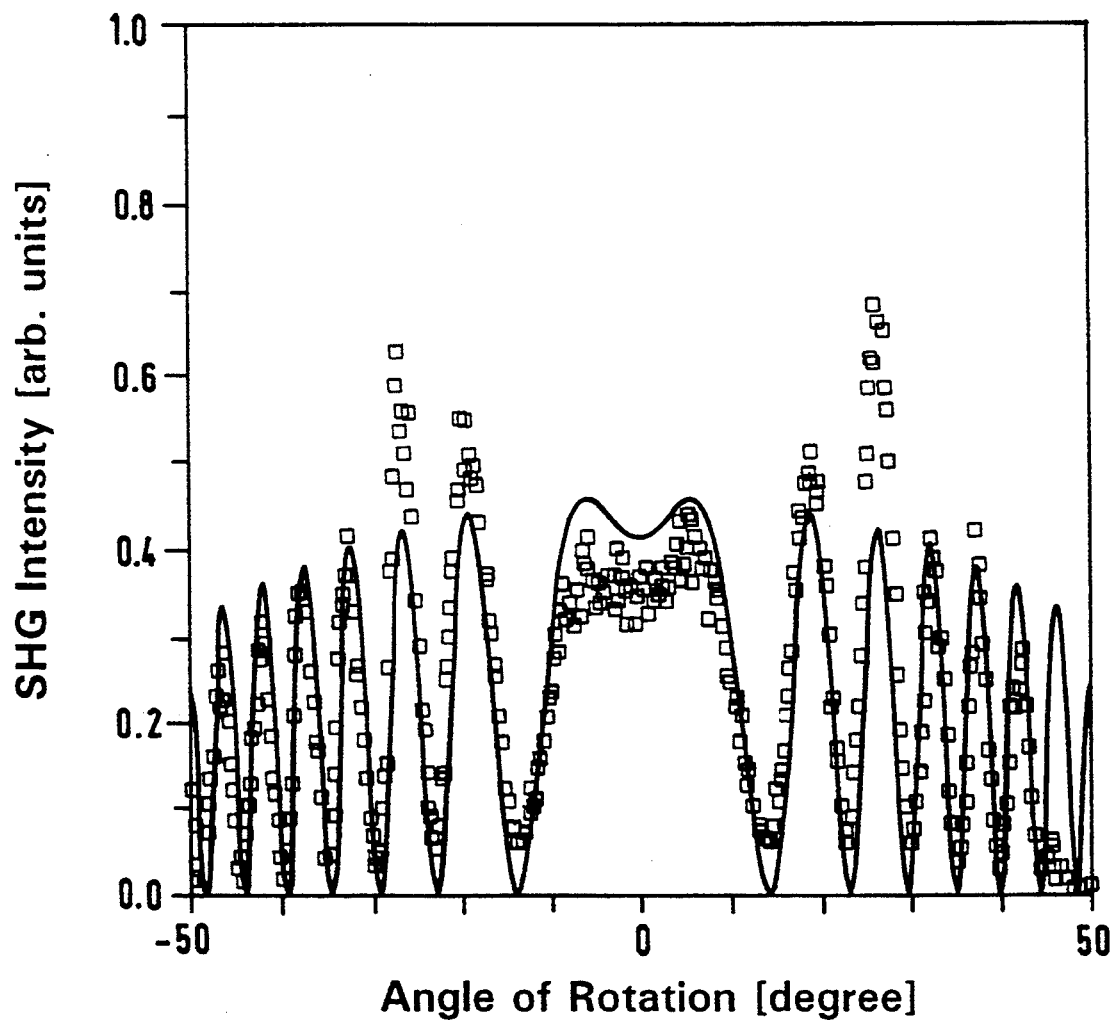
FIG. 6 shows a fringe pattern obtained by the Marker fringe method and the fitting curve thereof.

Jerphagnon and S. K. Kurtz, J. Appl. Phys., Vol. 41, pp. 1667-1681 (1970). The light source was a pulsed Nd:YAG laser having a wavelength of 1064 nm. The second harmonic wave were passed through a 532-nm interference filter and the optical intensity was detected by a photomultiplier tube. The fringes produced were subjected to curve fitting using the refractive index data obtained in Example 4. The results are shown in FIG. 6, in which the small circles indicate the observed values of the SHG intensity and the solid line is the result of curve fitting. The SHG intensity measurement was also conducted on a standard sample of quartz crystal ($d_{11}=0.335$ pm/V) and comparison was made with the result shown in FIG. 6. As a result, the molecular crystal of the present invention was found to have the non-linear optical coefficient $d_{22}$ of 53 pm/V.

EXAMPLE 6

The compound of the formula (I) was dissolved in acetonitrile to prepare a saturated solution, which was held at 20° C. in a thermostatic bath. An end of a hollow glass fiber (inner diameter=1 microns) was dipped in the saturated solution. The solution was sucked up into the glass fiber by capillarity. The glass fiber was held in this state to allow acetonitrile to evaporate and a single crystal grew within the fiber. It was confirmed by observation under a polarizing microscope that the crystal had a good alignment of crystallographic orientation along the longitudinal direction of the fiber for a length of at least about 15 mm. Both ends of the glass fiber were cut off with a fiber cutter and the cut surfaces were polished to fabricate a fiber waveguide-type optical wavelength conversion device.

Light from a Nd:YAG laser having a wavelength of 1064 nm was guided into the optical wavelength conversion device and the green-colored second harmonic wave was generated. Similarly, the blue-colored second harmonic wave was generated when light from a dye laser having a wavelength of 860 nm was guided into the optical wavelength conversion device. In either case, no observable damage to the crystal occurred as a result of the irradiation of laser light.

EXAMPLE 7

Figure 7:
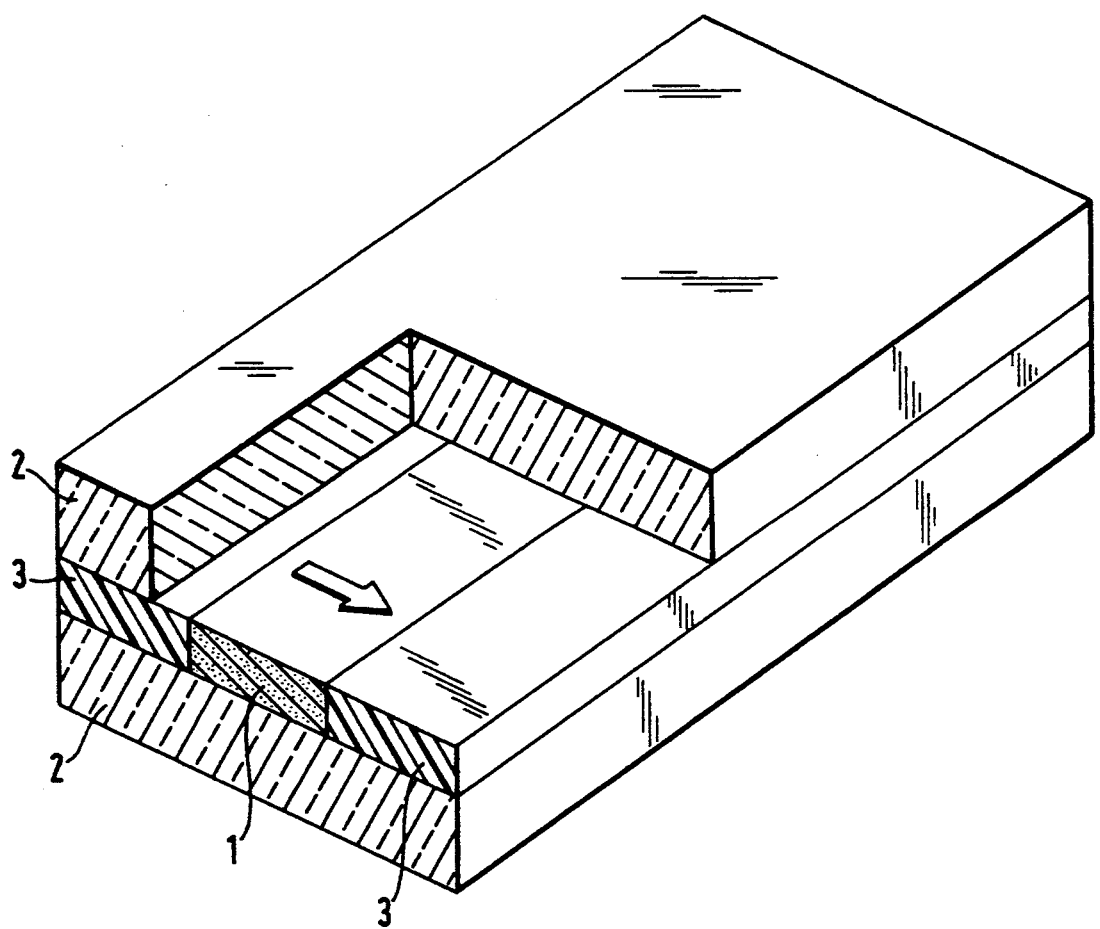
FIG. 7 is a structure of a slab waveguide-type optical wavelength conversion device.
Figure 8:
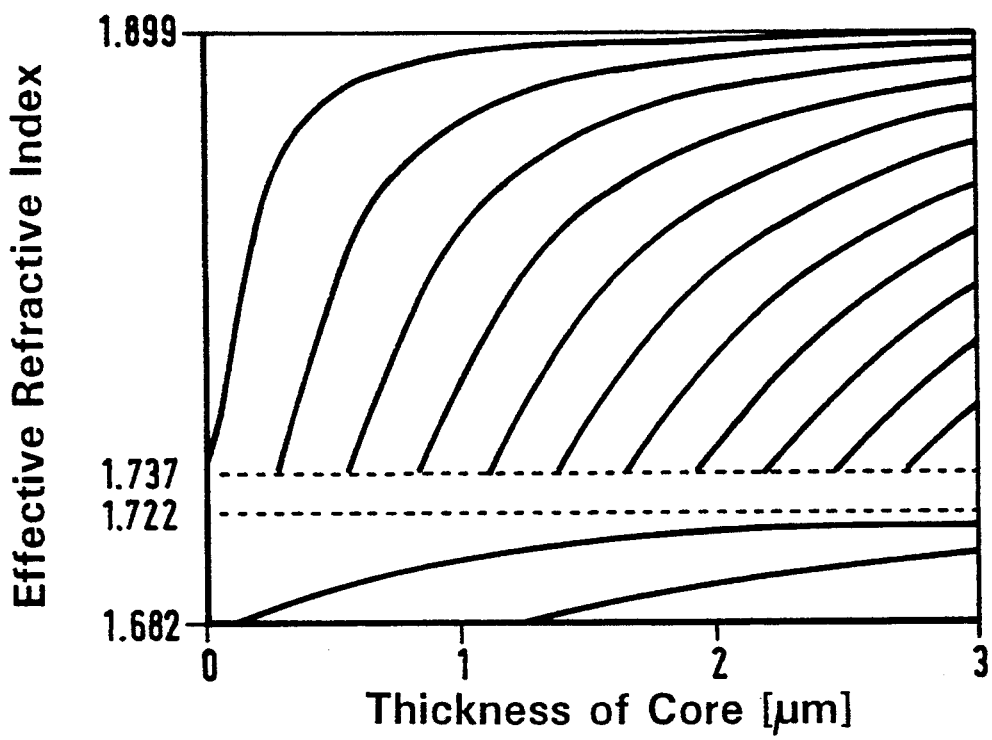
FIG. 8 shows TE mode dispersion curves for a slab waveguide-type optical wavelength conversion device.

A slab waveguide-type optical wavelength conversion device having the structure shown in FIG. 7 was fabricated. The core 1 was the crystal of the compound of the formula (I). The clad 2 was made of high refractive index glass SF 15. FIG. 8 shows TE mode dispersion curves for a fundamental wave having a wavelength of 830 nm. These curves, as well as the relation $N(\omega)<n_{clad}(\omega)$ [see M. Umegaki, "Yuki Hisenkei Kogaku Zairyo (Organic Nonlinear Optical Materials)", Bunshin Publishing (1990)]show that, under given any values of core thickness (crystal thickness), the second harmonic wave can be generated by the Cherenkov-type phase matching. In the relation set forth above, $N(\omega)$ represents the effective refractive index of the fundamental wave and $n_{clad}(2\omega)$ represents the refractive index of the second harmonic wave in the clad. In FIG. 8, $n_{core}$(830 nm) is 1,722, $n_{core}$(415 nm) is 1.899, $n_{clad}$(830 nm) is 1,682 and $n_{clad}$(415 nm) is 1,737, respectively. For achieving a large optical confining effect, it is advantageous to reduce the core thickness. Hence, the core 1 (with a thickness of about 40 microns) was made thinner to a thickness of about 3 microns by liquid-phase etching with a mixed solvent system of acetone and acetonitrile, whereby a slab waveguide-type optical wavelength conversion device was fabricated. The gap between the upper and lower clad layers was filled with an adhesive polymer 3 (acrylic UV-curable resin), thereby fixing the core 1 in position. The arrow on the core 1 designates the direction of the large d tensor element ($d_{22}$) which is parallel to the Y axis. Light from a Nd:YAG laser having a wavelength of 1064 nm which was polarized in the direction of Y axis (in TE mode) was guided into the optical wavelength conversion device and the green-colored second harmonic wave was generated. Similarly, the blue-colored second harmonic wave was generated when light from a dye laser having a wavelength of 860 nm (TE mode) was guided as the fundamental wave into the optical wavelength conversion device. In either case, no observable damage to the crystal occurred as a result of the irradiation of laser light.

EXAMPLE 8

Figure 9:
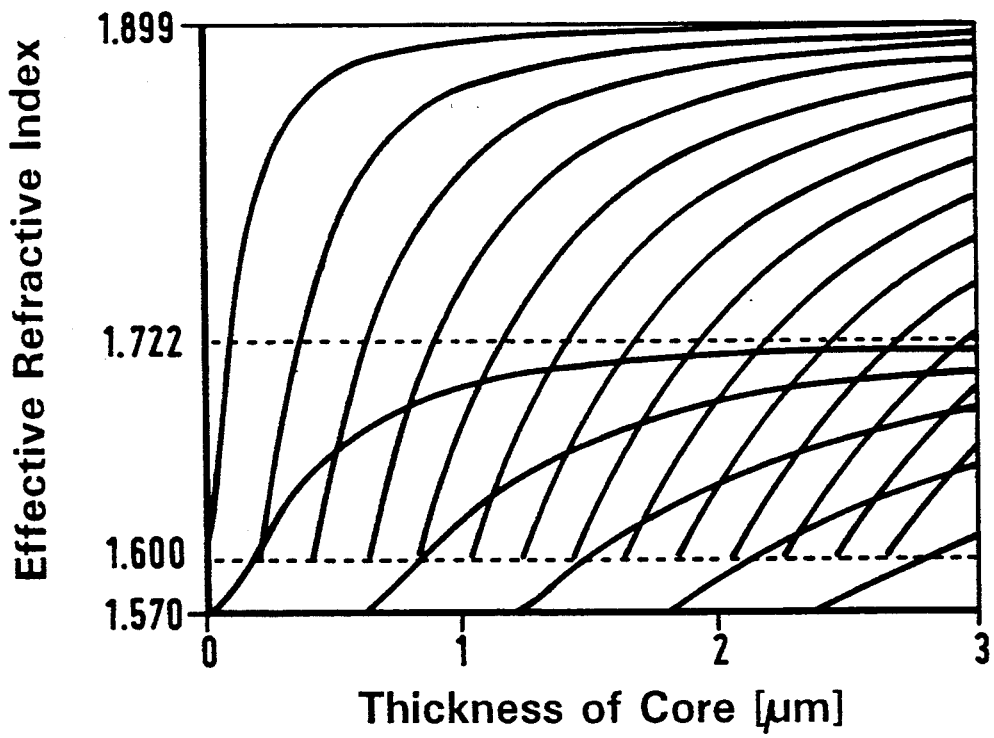
FIG. 9 shows TE mode dispersion curves for another slab waveguide-type optical wavelength conversion device.

A slab waveguide-type optical conversion device having the same structure shown in FIG. 7 was fabricated. The core was the crystal of the compound of the formula (I) and an acrylic UV-curable resin was used as the clad. The crystal was made thinner to a thickness of about 2.5 microns by liquid-phase etching with a mixed solvent system of acetone and acetonitrile. FIG. 9 shows TE mode dispersion curves in the thus fabricated optical wavelength conversion device for a fundamental wave having a wavelength of 830 nm. In FIG. 9, $n_{core}$(830 nm) is 1.722, $n_{core}$(415 nm) is 1.899, $n_{clad}$(830 nm) is 1.570 and $n_{clad}$(415 nm) is 1.600, respectively. Light from a dye laser having wavelengths of 830 to 900 nm (TE mode) was guided into the optical wavelength conversion device and the blue-colored second harmonic wave was generated. Generally, the change in the wavelength of incident light corresponds to the change in the core thickness. Thus, an experiment was conducted to scan the wavelength of the dye laser. As a result, the phase matching conditions have changed, causing the SHG intensity to change with wavelength. In either experiment, no observable damage to the crystal occurred as a result of the irradiation of laser light.

EXAMPLE 9

Figure 10:
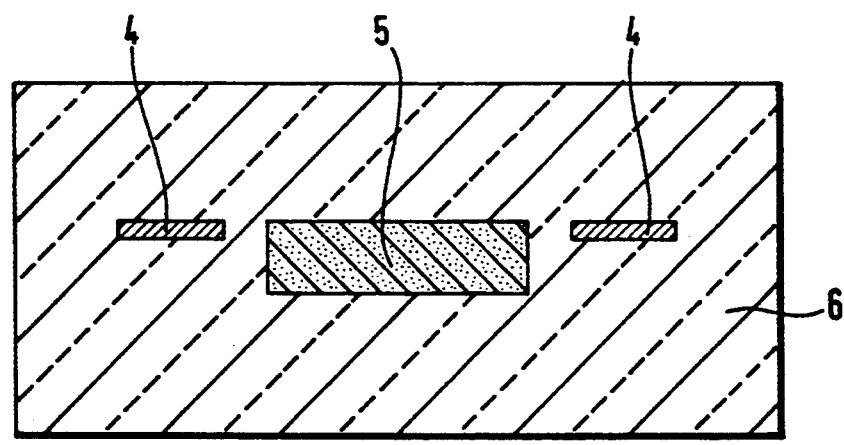
FIG. 10 shows a cross sectional view of the waveguide-type optical wavelength conversion device.

An optical wavelength conversion device was fabricated using as a clad material the molded acrylic UV-curable resin which was described in Example 8. The crystal of the compound of the formula (I) was adhered as a core onto the clad material. An acrylic UV-curable resin of the same material as the clad was used as an adhesive. In the next step, the thickness of the core was reduced to about 0.5 microns by subjecting it to an etching treatment. Subsequently, it was spin-coated with the UV-curable resin, having lower optical index than that of the crystal, to a thickness of about 3 microns. Then, the width of the core was reduced to 1 micron by subjecting it to a conventional lithographic process consisting of photoresist coating, exposure to light, development and etching. After that, it was again spin-coated with the UV-curable resin to a thickness of about 0.5 microns. Subsequently, a gold thin film was deposited thereon. The gold thin film was subjected to a conventional lithographic process so that the thin gold film was shaped to a pair of coplanar electrodes in such a manner that the core is located between the electrodes. Finally, the assembly was further spin-coated with the UV-curable resin to a thickness of about 6 microns. A cross-sectional view of the thus fabricated optical wavelength conversion device is shown in FIG. 10. In FIG. 10, reference numerals 4, 5 and 6 indicate the gold electrode, core of the crystal and clad of the UV-curable resin, respectively.

Light from a laser diode having a wavelength of 830 nm was introduced into this device under applying an AC field (10 V, 1 kHz) thereto. The blue-colored second harmonic wave was successfully modulated.

What is claimed is:

1. An organic molecular crystal comprising a compound represented by the following formula (I):

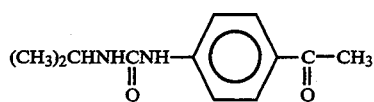

2. An optical wavelength conversion device comprising a single crystal of the organic molecular crystal according to claim 1.

3. A fiber waveguide-type optical wavelength conversion device comprising a core and a clad, wherein the organic molecular crystal according to claim 1 is used as the core.

4. The fiber waveguide-type optical wavelength conversion device according to claim 3, which further comprises a pair of electrodes which are provided in such a manner that the core is located between the electrodes.

5. A slab or channel waveguide-type optical wavelength conversion device comprising a core and a clad, wherein the organic molecular crystal according to claim 1 in a thin, planar form is used as the core.

6. The slab or channel waveguide-type optical wavelength conversion device according to claim 5, which further comprises a pair of electrodes which are provided in such a manner that the core is located between the electrodes.

* * * * *